United States Patent [19]

Hirai et al.

[11] 4,264,499
[45] Apr. 28, 1981

[54] 1-SUBSTITUTED THIOMETHYLTRIAZOLOBENZODIAZEPINES AND PRODUCTION THEREOF

[75] Inventors: Kentaro Hirai, Kyoto; Toshio Fujishita, Toyonaka; Teruyuki Ishiba, Takatsuki, all of Japan

[73] Assignee: Shionogi & Co., Ltd., Osaka, Japan

[21] Appl. No.: 110,842

[22] Filed: Jan. 10, 1980

Related U.S. Application Data

[62] Division of Ser. No. 16,615, Mar. 1, 1979, Pat. No. 4,231,930.

[30] Foreign Application Priority Data

Mar. 9, 1978 [JP] Japan ................................. 53-27524

[51] Int. Cl.³ ..................... A61K 31/55; C07D 487/04
[52] U.S. Cl. ............................. 260/245.5; 260/243.3; 260/245.7; 260/244.4; 424/244; 424/248.5; 424/251; 424/267; 544/122; 544/287; 548/262
[58] Field of Search ....................................... 260/245.5

[56] References Cited

U.S. PATENT DOCUMENTS 4,155,913  5/1979  Hellerbach et al. ............. 260/245.5

FOREIGN PATENT DOCUMENTS 7205705 10/1972 Netherlands .......................... 260/245.5

Primary Examiner—Alton D. Rollins
Attorney, Agent, or Firm—Wenderoth, Lind & Ponack

[57] ABSTRACT

A compound of the formula:

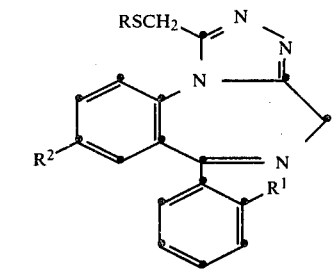

wherein
R is hydrogen, 2–5C alkoxycarbonyl, 1–7C acyl, 1–4C alkylthio, 7–10C phenylalkylthio, phenylthio, halo-phenylthio, disubstituted aminothio,

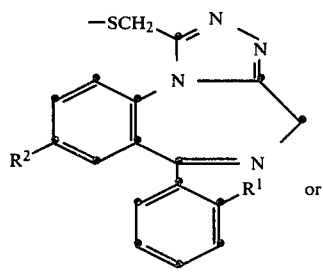

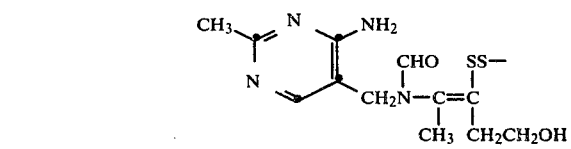

$R^1$ is hydrogen or halogen;
$R^2$ is halogen or nitro;
and its pharmaceutically acceptable acid addition salts.

The compounds and salts thereof are useful as psychotropic agents and as anxiolytics, anticonvulsants and hypnotics.

7 Claims, No Drawings

1-SUBSTITUTED THIOMETHYLTRIAZOLOBENZODIAZEPINES AND PRODUCTION THEREOF

This is a division of application Ser. No. 16,615, filed Mar. 1, 1979, now U.S. Pat. No. 4,231,930.

The present invention relates to 1-substituted thiomethyltriazolobenzodiazepines and production thereof. More particularly, this invention is directed to a compound of the formula:

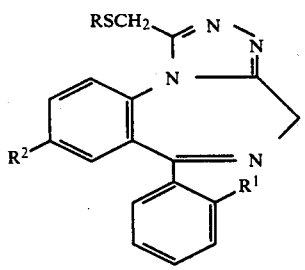

wherein

R is hydrogen, 2-5C alkoxycarbonyl, 1-7C acyl, 1-4C alkylthio, 7-10C phenylalkylthio, phenylthio, halo-phenylthio, disubstituted aminothio,

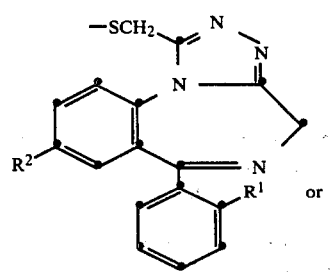

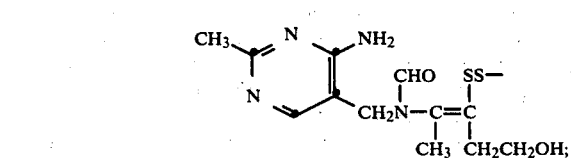

$R^1$ is hydrogen or halogen;

$R^2$ is halogen or nitro;

and its pharmaceutically acceptable acid addition salts.

Preferably compound (I) is a compound of the formula:

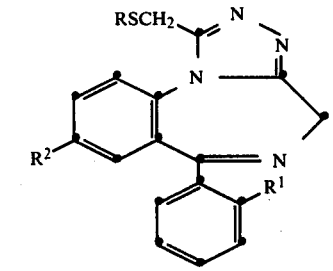

wherein

R is hydrogen, 2-5C alkoxycarbonyl, 1-7C acyl, t-butylthio, benzylthio, p-chlorophenylthio, morpholinothio,

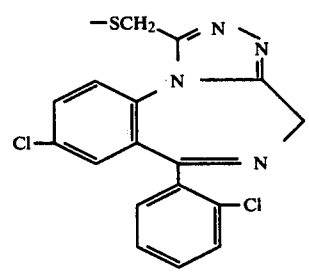

or

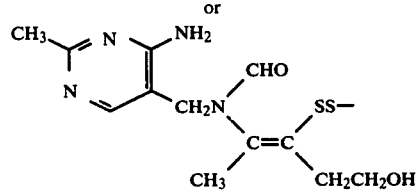

$R^1$ is chlorine or fluorine; and $R^2$ is chlorine.

Terms used in the definition of said product (I) are explained illustratively as follows:

alkoxycarbonyl (e.g. methoxycarbonyl, ethoxycarbonyl, propoxycarbonyl, isopropoxycarbonyl, butoxycarbonyl), acyl (e.g. formyl, acetyl, propionyl, butyryl, isovaleryl, benzoyl, cyclopropanecarbonyl, cyclohexanecarbonyl), alkylthio (e.g. methylthio, ethylthio, propylthio, isopropylthio, isobutylthio), phenylalkylthio (e.g. benzylthio, phenethylthio, phenylpropylthio), halo-phenylthio (e.g. bromophenylthio, chlorophenylthio, fluorophenylthio, iodophenylthio), disubstituted aminothio (e.g. morpholinothio, piperidinothio, pyrrolidinothio, dimethylaminothio, diethylaminothio) and halogen (e.g. chlorine, bromine, fluorine, iodine).

1-Alkylthiomethyl-triazolylbenzodiazepines are disclosed in Brit. Pat. No. 1,331,015, but said compounds (I) are not known yet.

The 1-substituted thiomethyl-triazolobenzodiazepines (I) are prepared as shown in the following scheme:

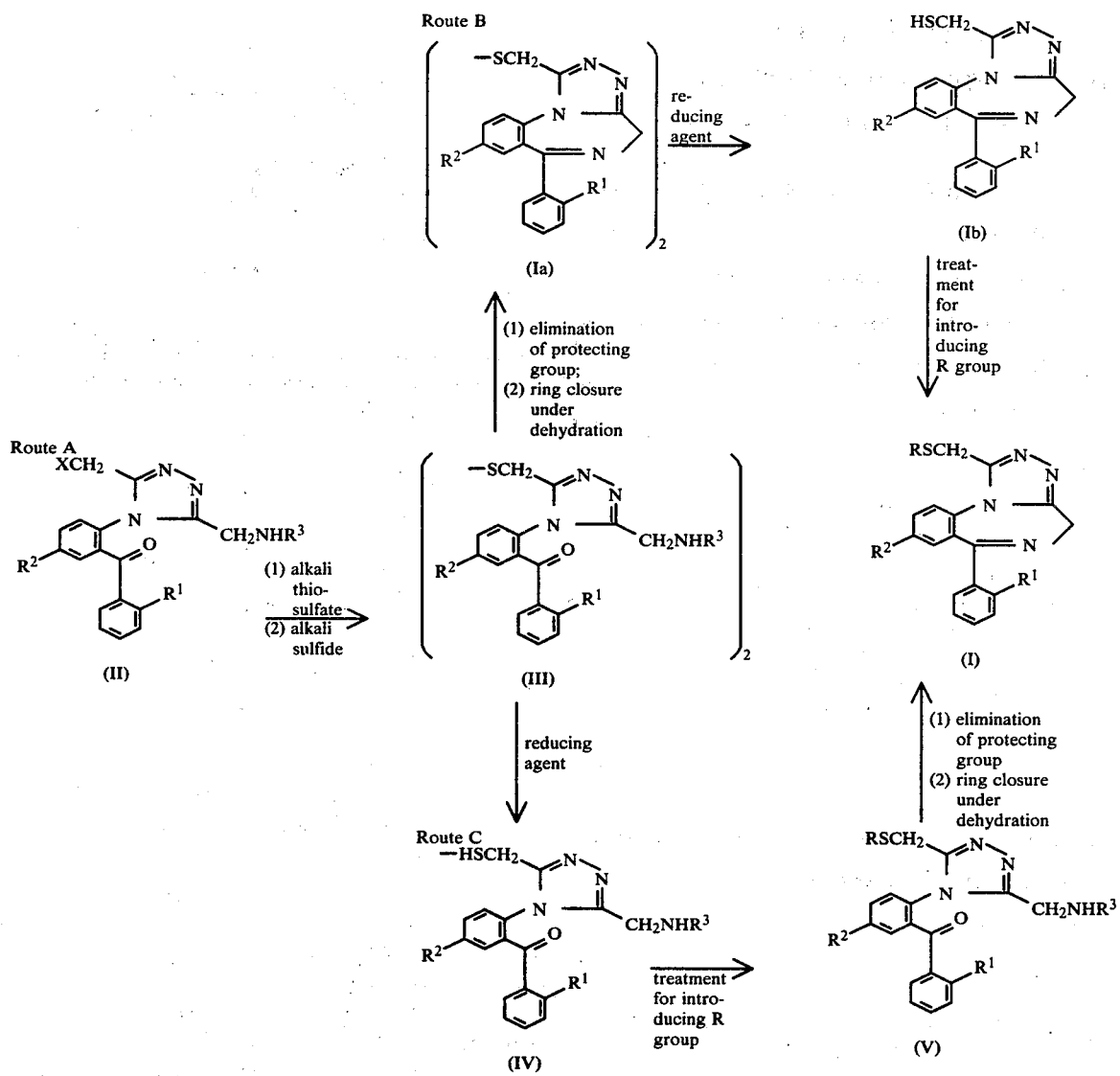

In this scheme $R^3$ is amino-protecting group (e.g. carbobenzoxy, t-butoxycarbonyl, p-methoxybenzyloxycarbonyl, trityl); X is halogen (e.g. chlorine, bromine, iodine); and R, $R^1$ and $R^2$ have each the same significance as given earlier.

Route A

This reaction consists in reacting the halomethyltriazole compound (II) with an alkali thiosulfate to give an alkali thiosulfuric ester and reacting the said ester with an alkali sulfide to afford the disulfide (III). In general, the reaction is carried out at room temperature in an aqueous solvent. The alkali thiosulfate includes sodium thiosulfate and potassium thiosulfate. The alkali sulfide includes alkali arylsulfide (e.g. sodium phenylsulfide), alkali arakylsulfide (e.g. sodium benzylsulfide), and thiol type thiamine alkali metal (e.g. sodium, potassium salt).

Route B

The disulfide (III) obtained in said Route A is subjected to deprotection to afford an aminomethyl compound, then this aminomethyl compound is subjected to ring closure under dehydration, whereby the triazolobenzodiazepin-1-ylmethyl disulfide (Ia) is produced. The deprotection may be carried out in a conventional manner for elimination of amino protecting groups which has been known in the field of peptide synthesis. For example, carbobenzoxy, t-butoxycarbonyl, p-methoxybenzyloxycarbonyl and the like may be subjected to a method using acetic acid/hydrobromic acid or trifluoroacetic acid or to a catalytic reduction under hydrogen stream; trityl may be subjected to a method using dilute acetic acid. In each case the reaction may be carried out appropriately at room temperature or under heating. Ring closure dehydration under for producing the triazolobenzodiazepine ring may be carried out in an appropriate inert solvent (e.g. dimethylformamide, dimethylsulfoxide, hexamethylphosphoric triamide) at room temperature or under heating, ordinarily in the range of temperature from 20° to 200° C.

Further, the disulfide (Ia) is treated with a reducing agent to afford the thiol (Ib). The reducing agent illustratively includes L-cysteine, dithiothreitol, 2-mercaptoethanol and thioglycolic acid. This reaction may be carried out in an appropriate inert solvent (e.g. methylene chloride, methanol, ethanol, dimethylformamide) at room temperature.

Moreover, the thiol (Ib) can, if necessary, be subjected to treatment for introducing R group to afford the product (I) which has various substitutents. The R group-introducing agent includes illustratively N-substituted phthalimide (e.g. N-(benzylthio)phthalimide, N-(p-chlorophenylthio)phthalimide, N-(t-buthylthio)phthalimide), N-(halogenothio)amine (e.g. 4-(bromothio)morpholine, 1-(chlorothio)piperidine, 1-(bromothio)pyrrolidine, N-bromothiodimethylamine, N-chlorothiodiethylamine), S-(4-morpholino)thiamine disulfide, acetic anhydride, propionic anhydride, benzoic anhydride, ethyl chlorocarbonate and the like. This reaction may be carried out in an appropriate solvent (e.g. methylene chloride, chloroform, methanol, ethanol, dimethylformamide, pyridine, triethylamine, hexamethylphosphoric triamide) at room temperature or under cooling or heating in a conventional manner.

Route C

The disulfide (III) obtained in said Route A is treated with a reducing agent to afford the thiol (IV). Then the thiol is subjected to R group-introducing treatment to afford the sulfide (V). Further the sulfide is subjected to elimination of the protecting group and ring closure under dehydration to produce the triazolobenzodiazepine ring, whereby the product (I) is obtained. Each reaction can be carried out in the same manner as those of above Route B.

The stating material (II) used in Route A can, for example, be prepared in the following scheme:

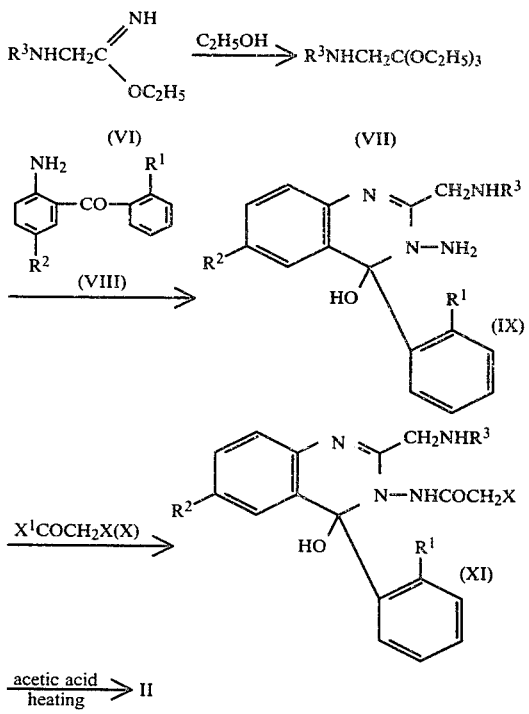

wherein $X^1$ is halogen; $R^1$, $R^2$, $R^3$ and X each is as defined above.

For the purpose of preparation, crystallization, improvement on stability or the like, the product (I) may be converted into a pharmaceutically acceptable acid addition salt of inorganic acid (e.g. hydrochloric acid, sulfuric acid, nitric acid, phosphoric acid, thiocyanic acid or the like) or organic acid (e.g. acetic acid, succinic acid, oxalic acid, maleic acid, malic acid, phthalic acid or the like).

The objective compound (I) or its acid addition salts may be applied in enteral or parenteral route singly or in combination with ordinary pharmaceutical carriers such as wheat starch, corn starch, potato starch, gelatin or water. Choice of carriers can be determined in accordance with route of administration, solubility of main ingredient, pharmaceutical standard adopted and the like. Pharmaceutical preparation includes tablets, capsules, pills, suspensions, syrups, powders, granules, solutions, suppositories and the like. These preparations can be formulated in a conventional manner for pharmaceutical preparation. A dosage of the product (I) or its acid addition salt for a human adult is about 0.25 mg to about 10 mg per day.

Thus obtained triazolobenzodiazepines (I) and their acid addition salts are useful as psychotropic agents such as anxiolytics, anticonvulsants, hypnotics or their synthetic intermediates, showing excellent psychotropic activities, in particular sedative, anticonvulsive, hypnotic, muscle relaxant activities or the like. For example, 8-chloro-1-(ethoxycarbonylthio)methyl-6-(2-chlorophenyl)-4H-s-triazolo[4,3-a][1,4]benzodiazepine showed $ED_{50}$ 0.17 mg/kg (mouse, per os.) in anticonvulsive activity (pentylenetetrazole). Other compounds showed similar pharmacological activities, too.

EXAMPLE 1

(1) To a solution of 2′,5-dichloro-2-(5-carbobenzoxyaminomethyl-3-chloromethyl-1,2,4-triazol-4-yl)benzophenone (12.8 g) in ethanol (600 ml) is added a solution of sodium thiosulfate (7.2 g) in water (200 ml), and the resultant mixture is refluxed for 1.5 hours. The reaction mixture is evaporated under reduced pressure to remove the solvent, whereby 2′,5-dichloro-2-(3-carbobenzoxyaminomethyl-5-mercaptomethyl-1,2,4-triazol-4-yl)-benzophenone thiosulfate monosodium salt is obtained. This substance is dissolved in water (600 ml), mixed with thiol type thiamine sodium salt (10.8 g) and stirred overnight. The colorless precipitate is filtered, washed with water and dissolved in a mixture of chloroform and methanol. The organic layer is dried over sodium sulfate and the solvent is evaporated under reduced pressure. The residue is chromatographed on a column of silica gel, which is eluted with ethyl acetate to give bis[4-{2-(2-chlorobenzoyl)-4-chlorophenyl}-5-carbobenzoxyaminomethyl-1,2,4-triazol-3-methyl]disulfide (7.4 g) as crystals melting at 113°–115° C. This compound is recrystallized from ethyl acetate/n-hexane to give colorless crystals.

(2) A mixture of above product (39.3 g) and 25% hydrobromic acid-acetic acid solution (80 ml) is stirred to completely dissolve. The resultant solution is mixed with an excess of ether. The precipitate (hydrobromide) is washed twice with ether by decantation, dissolved in dimethylformamide (400 ml) and heated at 75° C. for 4 hours. The solvent is evaporated under reduced pressure from the reaction mixture and the residue is distributed with chloroform and aqueous sodium bicarbonate. The organic layer is washed with water, dried over sodium sulfate and the solvent is evaporated. The oily substance is crystallized from ethanol to give bis[8-chloro-6-(2-chlorophenyl)-4H-s-triazolo[4,3-a][1,4]benzodiazepine-1-ylmethyl] disulfide ethanolate (26.3 g) as crystals. This material is recrystallized from ethanol/methylene chloride to give crystals melting at 188° C.

EXAMPLE 2

To a solution of above product (800 mg), methylene chloride (12 ml), water (5 ml) and methanol (25 ml) is added L-cysteine (610 mg). The reaction mixture is stirred for 2 hours and the precipitated crystine is filtered off. The solvent is evaporated from the filtrate under reduced pressure and the residue is distributed with chloroform and water. The organic layer is dried over sodium sulfate and the solvent is evaporated. The viscous oily material is crystallized from ether to give 8-chloro-1-(mercaptomethyl)-6-(2-chlorophenyl)-4H-s-triazolo[4,3-a][1,4]benzodiazepine (725 mg) as crystals. This material is recrystallized from ethyl acetate to give colorless needles melting at 198°-200° C.

EXAMPLE 3

A solution of N-(benzylthio)phthalimide (1.1 g) in benzene (50 ml) is refluxed and a solution of 8-chloro-1-(mercaptomethyl)-6-(2-chlorophenyl)-4H-s-triazolo[4,3-a][1,4]benzodiazepine (700 mg) in methylene chloride (7 ml) is added at a stroke. The solvent is evaporated from the reaction mixture and the residue is chromatographed on a column of silica gel, which is eluted with ethyl acetatemethanol (20:1) to give 8-chloro-1-(benzylthio)methyl-6-(2-chlorophenyl)-4H-s-triazolo[4,3-a][1,4]benzodiazepine (350 mg) as crystals. This material is recrystallized from ethyl acetate to give crystals melting at 144°-145° C.

EXAMPLE 4-5

Using the following starting materials (Ib) and (XII), the reaction is carried out as in Example 3, whereby the corresponding product (I) is obtained:

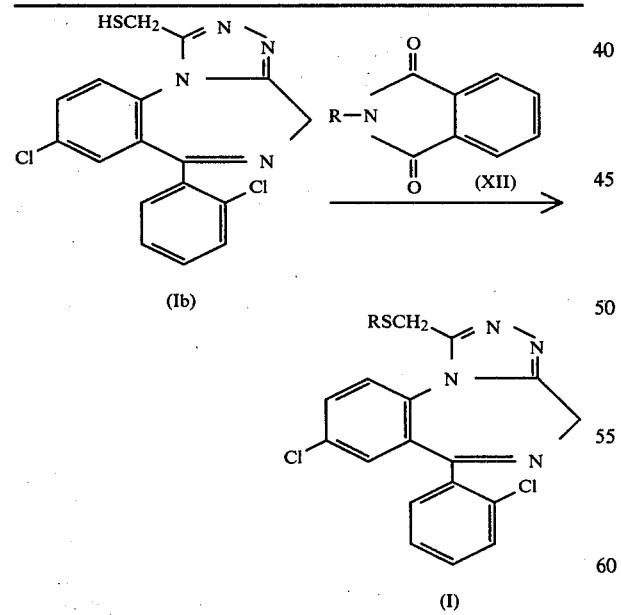

| Example No. | R | I NMR:$\delta^{CDCl_3}$ (ppm) |
|---|---|---|
| 4 | Cl—⟨⟩—S— | 4.33(s, 2H, CH$_2$SS)* 4.15, 5.50(2H, ABq J=14Hz, CH$_2$N=) |
| 5 | (CH$_3$)$_3$C—S— | 1.37(9H, s), 4.30, 4.60 (2H, ABq, J=13Hz), |

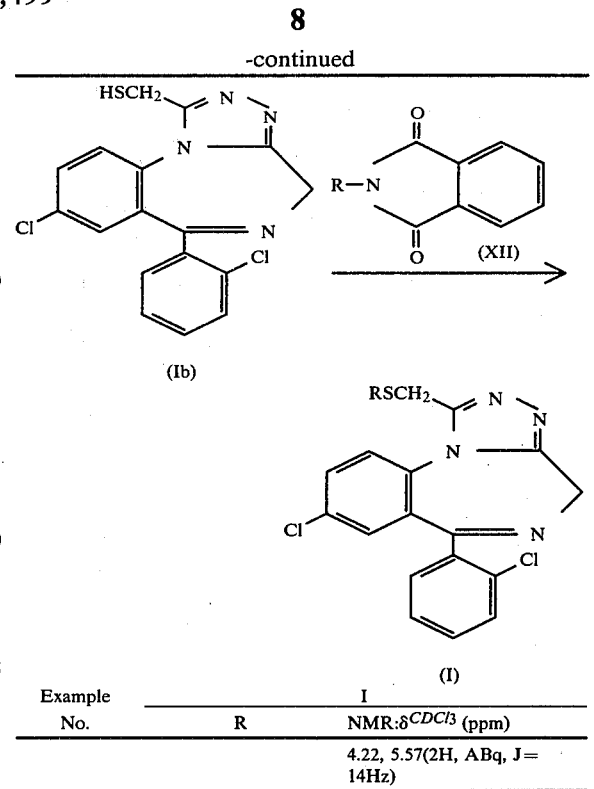

| Example No. | R | I NMR:$\delta^{CDCl_3}$ (ppm) |
|---|---|---|
|  |  | 4.22, 5.57(2H, ABq, J=14Hz) |

*Hydrochloride of this material shows crystals melting at 175-180° C.

EXAMPLE 6

(1) Using L-crysteine (0.6 g) a solution of bis[4-{2-(2-chlorobenzoyl)-4-chlorophenyl}-5-carbobenzoxyaminomethyl-1,2,4-triazol-3-methyl]disulfide (1.05 g), methanol (150 ml) and water (20 ml) the reaction is carried out as in Example 2 to give 2',5-dichloro-2-(5-carbobenzoxyaminomethyl-3-mercaptomethyl-1,2,4-triazol-4-yl)-benzophenone (0.85 g) as crystals melting at 153°-155° C.

(2) A solution of above product (1.0 g), acetic anhydride (2 ml) and pyridine (5 ml) is stirred overnight and the solvent is evaporated from the reaction mixture. The residue is distributed in ethyl acetate and aqueous sodium hydrogen carbonate. The organic layer is washed with water, dried over sodium sulfate and evaporated to remove the solvent. The residue is chromatographed on a column of silica gel, which is eluted with ethyl acetate to give 2',5-dichloro-2-(3-acetylthiomethyl-5-carbobenzoxyaminothiomethyl-1,2,4-triazol-4-yl)benzophenone (1.0 g) as a colorless oil.

IR (film) 3300, 1700 (broad), 1595 cm$^{-1}$ (3) Using the above product and 30% hydrobromic acid-acetic acid solution, the reaction is carried out as in Example 1 (2), whereby 8-chloro-1-(acetylthio)-methyl-6-(2-chlorophenyl)-4H-s-triazolo[4,3-a][1,4]benzodiazepine as crystals melting at 206°-208° C.

EXAMPLE 7

Using 8-chloro-1-(mercaptomethyl)-6-(2-chlorophenyl)-4H-s-triazolo[4,3-a][1,4]benzodiazepine (1.0 g), acetic anhydride (5 ml) and pyridine (5 ml), the reaction is carried out as in Example 6 (2), whereby 8-chloro-1-(acetylthio)methyl-6-(2-chlorophenyl)-4H-s-triazolo-[4,3-a][1,4]benzodiazepine (0.85 g) as crystals melting at 206°-208° C.

EXAMPLE 8

(1) To a solution of 2',5-dichloro-2-(5-carbobenzoxyaminomethyl-3-mercaptomethyl-1,2,4-triazol-4-yl)-benzophenone (0.5 g), triethylamine (0.5 ml) and methylene chloride (10 ml) is added a solution of ethyl chlorocarbonate (0.5 ml) in tetrahydrofuran (8 ml) at 15° C. with stirring. The reaction mixture is stirred for 1 hour and poured into water. The organic layer is washed with water, dried over sodium sulfate and evaporated to remove the solvent. The residual oily material is chromatographed on a column of silica gel, whereby 2',5-dichloro-2-(5-carbobenzoxyaminomethyl-3-ethoxycarbonylthiomethyl-1,2,4-triazol-4-yl)benzophenone (0.5 g) is obtained as a colorless oil.

NMR:$\delta^{CDCl_3}$ 1.2(3H, t, J=7 Hz, CH$_2$C$\underline{H}_3$), 3.8~4.4(6H, collapsed, m, C$\underline{H}_2$S, C$\underline{H}_2$CH$_3$, C$\underline{H}_2$NH), 4.93(2H, s, OC$\underline{H}_2$Ph), 6.13(1H, br, t, N$\underline{H}$)

(2) Using above product and 30% hydrogen bromide/acetic acid solution, the reaction is carried out as in Example 1 (2), whereby 8-chloro-1-(ethoxycarbonylthio)methyl-6-(2-chlorophenyl)-4H-s-triazolo[4,3-a][1,4]benzodiazepine is obtained as crystals melting at 184°-186° C. (decomp.).

EXAMPLE 9

Using 8-chloro-1-(mercaptomethyl)-6-(2-chlorophenyl)-4H-s-triazolo[4,3-a][1,4]benzodiazepine (1.0 g), triethylamine (10 ml), methylene chloride (10 ml), tetrahydrofuran (10 ml) and ethyl chlorocarbonate (1 ml), the reaction is carried out as in Example 8 (1), whereby 8-chloro-1-(ehoxycarbonylthio)methyl-6-(2-chlorophenyl)-4H-s-triazolo-[4,3-a][1,4]benzodiazepine (970 mg) is obtained as crystals melting at 184°-186° C. (decomp.).

EXAMPLES 10-11

Using the following starting materials (IV) and (XIII), the reaction is carried out as in Example 6 (2) and (3), whereby the corresponding product (V) and (I) are obtained:

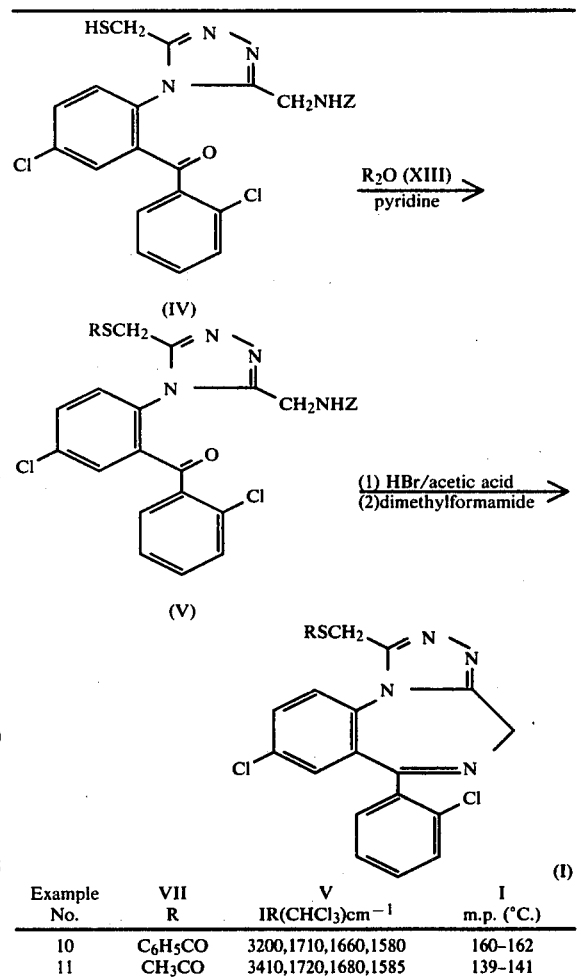

| Example No. | VII R | V IR(CHCl$_3$)cm$^{-1}$ | I m.p. (°C.) |
|---|---|---|---|
| 10 | C$_6$H$_5$CO | 3200,1710,1660,1580 | 160-162 |
| 11 | CH$_3$CO | 3410,1720,1680,1585 | 139-141 |

Note: Z means carbobenzoxy.

EXAMPLE 12

To a solution of 8-chloro-1-(mercaptomethyl)-6-(2-chlorophenyl)-4H-s-triazolo[4,3-a][1,4]benzodiazepine (1.5 g) in methylene chloride (20 ml) is added a solution of 4-(bromothio)morpholine (prepared from 0.47 g of dimorpholinodisulfide) in chloroform at −13° to −20° C., and the resultant mixture is stirred for 1.5 hours. The reaction mixture is mixed with water. The methylene chloride layer is separated, dried and evaporated to remove the solvent. The residue is crystallized from ether and filtered to give 8-chloro-1-(morpholinodithio)methyl-6-(2-chlorophenyl)-4H-s-triazolo[4,3-a][1,4]benzodiazepine (1.45 g) as crystals. This material is recrystallized from ethanol to give crystals melting at 149°-155° C. (decomp.).

EXAMPLE 13

To a solution of 8-chloro-1-(mercaptomethyl)-6-(2-chlorophenyl)-4H-s-triazolo[4,3-a][1,4]benzodiazepine (0.75 g), methanol (30 ml) and 15.3% ethanol-hydrochloric acid (1.43 g) is added the following compound (XIV) and the resultant mixture is stirred for 1.5 hours. The reaction mixture is mixed with aqueous sodium bicarbonate and the precipitated powder is filtered and extracted with chloroform. The organic layer is dried and the solvent is evaporated. The residue is solidified with ether to give the following compound (XV) (0.8 g) as powders melting at 130°–140° C.

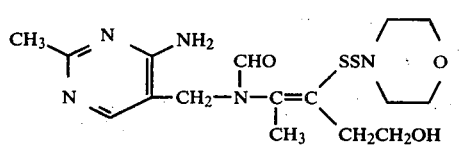

(XIV)

N-(2-methyl-4-aminopyrimidin-5-yl)-N-(4-hydroxy-1-methyl-2-morpholinodithio-1-butenyl)-formamide

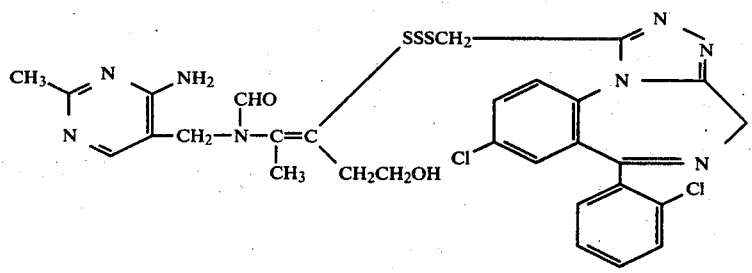

N-(2-methyl-4-aminopyrimidin-5-yl)-N-[4-hydroxy-1-methyl-2-{8-chloro-6-(2-chlorophenyl)-4H-s-triazolo[4,3-a][1,4]-benzodiazepine-1-ylmethyltrithio}-1-butenyl]formamide.

EXAMPLE 14

(1) Using 2'-fluoro-5-chloro-2-(3-carbobenzoxyaminomethyl-5-chloromethyl-1,2,4-triazol-4-yl)benzophenone, sodium thiosulfate and thiol type thiamine sodium salt, the reaction is carried out as in Example 1 (1), whereby bis[4-{2-(2-fluorobenzoyl)-4-chlorophenyl}-5-carbobenzoxyaminomethyl-1,2,4-triazol-3-methyl]disulfide is obtained.

(2) Using above product, 25% hydrobromic acid-acetic acid and dimethylformamide, the reaction is carried out as in Example 1 (2), whereby bis[8-chloro-6-(2-fluorophenyl)-4H-s-triazolo[4,3-a][1,4]benzodiazepine-1-ylmethyl]disulfide is obtained as crystals melting at 210°–213° C.

EXAMPLE 15

Using above product and L-cysteine, the reaction is carried out as in Example 2, whereby 8-chloro-1-(mercaptomethyl)-6-(2-fluorophenyl)-4H-s-triazolo-[4,3-a][1,4]benzodiazepine is obtained as crystals melting at 172°–175° C.

EXAMPLE 16

Using 8-chloro-1-(mercaptomethyl)-6-(2-fluorophenyl-4H-s-triazolo[4,3-a][1,4]benzodiazepine and ethyl chlorocarbonate, the reaction is carried out as in Example 8 (1), whereby 8-chloro-1-(ethoxycarbonylthio)-methyl-6-(2-fluorophenyl)-4H-s-triazolo[4,3-a][1,4]benzodiazepine is obtained as crystals melting at 154°–156° C.

What we claim is:

1. A compound of the formula:

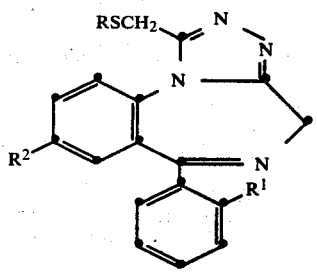

(XV)

wherein
R is 2–5C alkoxycarbonyl, 1–7C hydrocarbon carbonyl;
$R^1$ is hydrogen or halogen;
$R^2$ is halogen or nitro;
and its pharmaceutically acceptable acid addition salt.

2. A compound according to claim 1, in which
$R^1$ is chlorine or fluorine;
and $R^2$ is chlorine.

3. A compound according to claim 1, namely 8-chloro-1-(mercaptomethyl)-6-(2-chlorophenyl)-4H-s-triazolo[4,3-a][1,4]benzodiazepine.

4. A compound according to claim 1, namely 8-chloro-1-(acetylthio)methyl-6-(2-chlorophenyl)-4H-s-triazolo[4,3-a][1,4]benzodiazepine.

5. A compound according to claim 1, namely 8-chloro-1-(ethoxycarbonylthio)methyl-6-(2-chlorophenyl)-4H-s-triazolo-[4,3-a][1,4]benzodiazepine.

6. A compound according to claim 1, namely 8-chloro-1-(ethoxycarbonylthio)methyl-6-(2-fluorophenyl)-4H-s-triazolo-[4,3-a][1,4]benzodiazepine.

7. A compound according to claim 2, namely 8-chloro-1-(benzoylthio)methyl-6-(2-chlorophenyl)-4H-s-triazolo-[4,3-a][1,4]benzodiazepine.

* * * * *